United States Patent [19]

Melton

[11] 4,344,828

[45] Aug. 17, 1982

[54] ENERGY EFFICIENT DISTILLATION APPARATUS

[76] Inventor: James D. Melton, P.O. Drawer 206, Shelby, N.C. 28150

[21] Appl. No.: 297,852

[22] Filed: Aug. 31, 1981

Related U.S. Application Data

[63] Continuation-in-part of Ser. No. 115,904, Jan. 28, 1980, abandoned.

[51] Int. Cl.³ .............................................. B01D 3/02
[52] U.S. Cl. ...................................... 203/19; 203/24; 203/26; 203/DIG. 13
[58] Field of Search ........................ 203/19, 21, 22, 24, 203/26, DIG. 13; 62/40, 442; 202/176, 177, 179, 198, 232, 235

[56] References Cited

U.S. PATENT DOCUMENTS

| | | | |
|---|---|---|---|
| 2,242,926 | 5/1941 | Shipman | 62/442 |
| 2,490,152 | 12/1949 | Oaks | 203/22 |
| 3,234,109 | 2/1966 | Lustenaper | 203/22 |
| 3,893,894 | 7/1975 | Humiston | 202/235 |
| 4,094,655 | 6/1978 | Krieger | 62/40 |

*Primary Examiner*—Frank Sever
*Attorney, Agent, or Firm*—Bell, Seltzer, Park & Gibson

[57] ABSTRACT

An energy efficient distillation method is provided which is particularly adapted for use on a dairy farm, and which comprises a distilland evaporating receptacle, a distillate condensing receptacle, and a conduit interconnecting the evaporating receptacle and the condensing receptacle. A vacuum pump is provided for drawing a partial vacuum within the evaporating receptacle, and a vapor compression refrigeration system is provided which includes condenser coils disposed to heat and vaporize the distilland while it is within the evaporating receptacle, and evaporator coils for cooling and condensing the vaporized distilland in the condensing receptacle. A cooling distribution system is also provided whereby a variable portion of the cooling potential of the refrigeration system may be selectively directed to each of the condensing receptacle, a distillate receiver tank, or to a bulk milk container as utilized on a dairy farm or the like.

7 Claims, 1 Drawing Figure

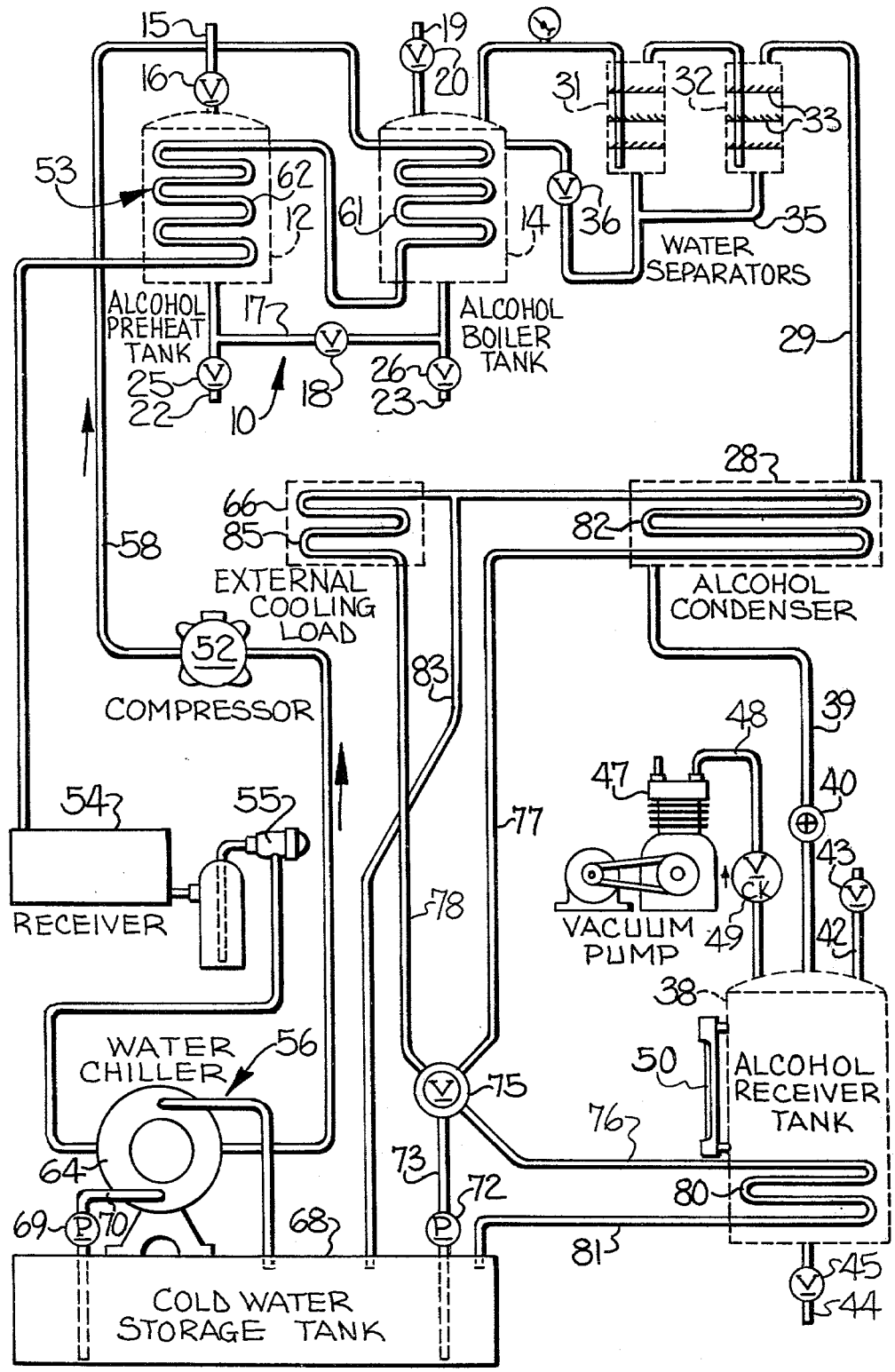

ENERGY EFFICIENT DISTILLATION APPARATUS

This application is a continuation-in-part of copending application Ser. No. 115,904 filed Jan. 28, 1980, now abandoned.

The present invention relates to an energy efficient distillation method useful in the production of alcohol for fuel, as well as the distillation of other liquids.

With the continuing depletion of hydrocarbon fuel sources, the development of alternate sources of energy from renewable raw materials is receiving increased attention. One such alternate energy source involves the production of alcohol by the fermentation process. Present fermentation processes include a distillation operation to purify and concentrate the alcohol, and wherein the grain mash is initially heated by steam coils or the like to vaporize the alcohol, with the resulting vapor being condensed in a water cooled condenser. As will be apparent, the distillation process involves the use of a substantial amount of energy, both to initially heat the mash and to cool and condense the resulting alcohol vapor.

It is accordingly an object of the present invention to provide an energy efficient method and apparatus for the distillation of a liquid, useful for example in the production of alcohol for a fuel.

It is a more particular object of the present invention to provide a method and apparatus for distilling alcohol or the like, and which efficiently utilizes the normally unrecovered heat produced by a conventional vapor compression refrigeration system to heat the mash, and which is also adapted to utilize at least a portion of the cooling potential of the refrigeration system to cool and condense the vaporized alcohol.

It is still another object of the present invention to provide a method and apparatus of the above-described type, and wherein the cooling potential of the vapor compression refrigeration system may be utilized to provide cooling to an external load, as well as cooling to facilitate the condensation of the vaporized alcohol.

In the disclosed specific embodiment, the invention finds particular utility on a dairy farm, in that all of the essential raw materials are usually present, and all of the resulting products and energy may be efficiently utilized at the farm. In particular, the grain which is normally fed to the cattle may be utilized as the distilland, and the resulting distillation or still product (commonly known as distillers grain) may be used as a high protein cattle feed and immediately fed to the cattle while wet, thus eliminating the normally required drying of the product. Further, the alcohol produced by the system may be used as a fuel on the farm, and a portion of the cooling potential of the refrigeration system may be utilized for bulk milk cooling.

These and other objects and advantages of the present invention are achieved in the embodiment illustrated herein by the provision of a distillation apparatus which comprises a distilland evaporating receptacle, a distillate condensing receptacle, a conduit interconnecting the evaporating receptacle and the condensing receptacle to permit vaporized distilland to pass therebetween, means for drawing a partial vacuum within the evaporating receptacle to lower the boiling temperature of the distilland therein, and a vapor compression refrigeration system including condenser means for heating and vaporizing the distilland while it is within the evaporating receptacle, and evaporator means for cooling and condensing the vaporized distilland in the condensing receptacle.

In the preferred embodiment, the apparatus further comprises a condensate receiver tank operatively connected to the condensing receptacle to receive the condensate therefrom, and the vacuum source is connected directly to the receiver tank, whereby the partial vacuum extends from the receiver tank through the condensing receptacle and to the evaporating receptacle. The apparatus also preferably includes cooling distribution means for selectively directing a variable portion of the cooling potential of the vapor compression refrigeration system to each of the condensing receptacle, the condensate receiver tank, and an external cooling load.

Some of the objects having been stated, other objects will appear as the description proceeds, when taken in connection with the accompanying drawing, which is a schematic representation of a distillation apparatus embodying the features of the present invention. The drawing shows the best mode of the invention.

Referring more specifically to the drawing, there is schematically illustrated an apparatus for the distillation of alcohol for use as a fuel, and which includes distilland evaporating receptacle means 10, wherein the grain mash is heated and vaporized as further described below. The receptacle means 10 comprises an alcohol preheater tank 12, and a separate boiler tank 14. The mash is delivered to the preheater tank through the entry line 15, which includes a valve 16. From the preheater tank, the mash or alcohol is delivered to the boiler tank through the conduit 17, when the valve 18 therein is open.

The boiler tank 14 includes an entry line 19 and valve 20 for periodically admitting a cleaning fluid to the tank, and cleaning fluid may also be admitted into the tank 12 via the line 15. Each tank includes a drain line 22, 23, and associated valve 25, 26, respectively, for removing such cleaning fluid, as well as to permit periodic removal of the distillation product (i.e., distillers grain).

The distillation apparatus further includes a distillate condensing receptacle or condenser 28, wherein the vaporized alcohol is cooled and condensed. The condenser 28 is connected to the boiler tank 14 via the conduit 29, and a pair of water separators 31, 32 are disposed in the conduit 29. The water separators each include a plurality of vanes 33 in the nature of twisted fan blades, for collecting condensed water vapor. The vaporized alcohol passes through the vanes, and the condensed water drips to the bottom of each separator where it collects. Since the collected water will have a relatively significant amount of alcohol dissolved therein, it is desirable to recirculate the collected water to the boiler tank 14 to permit recovery of this dissolved alcohol. For this purpose, a drain line 35 and valve 36 are provided for periodically delivering the collected water to the boiler tank. This water collects in the bottom of the boiler tank, and is periodically removed through the valve 26 when the system is shut down.

An alcohol receiver tank 38 is positioned below the alcohol condenser, and is connected thereto by a line 39 which has a sight glass 40 therein to permit visual monitoring of the flow of alcohol. The receiver tank 38 includes a separate entry line 42 and valve 43, to permit periodic entry of a cleaning fluid or the like, and a drain line 44 and valve 45 to permit periodic removal of the alcohol, or the cleaning fluid. In addition, a vacuum pump 47 is operatively connected to the receiver tank via the air line 48 which includes a one way check valve 49. Operation of the pump 47 is preferably automatically controlled by a pressure actuated switch (not shown) in the tank 38 whereby a predetermined partial vacuum is maintained in the tank. The tank 38 may further include a sight glass 50 to permit visual monitoring of the alcohol level therein.

The apparatus of the present invention further includes a vapor compression refrigeration system for heating and vaporizing the distilland (i.e. alcohol mash) while it is within the evaporating receptacle means 10, and for cooling and condensing the vaporized distilland in the condenser 28. More particularly, the refrigeration system includes a compressor 52 for raising the pressure and temperature of a gaseous refrigerant, a condenser generally indicated at 53 for cooling and liquifying the refrigerant, a receiver 54 for storing the liquid refrigerant, an expansion valve 55 for regulating the flow and reducing the pressure of the liquid refrigerant, evaporator means generally indicated at 56 for absorbing heat to boil the liquid refrigerant, and thereby producing a cooling potential, and a refrigerant conduit 58 for serially conveying a refrigerant through the above mentioned components and back to the compressor 52.

The condenser 53 of the refrigeration system comprises a first coil segment 61 operatively disposed within the boiler tank 14, and a second coil segment 62 positioned downstream of the first segment and operatively disposed within the preheater tank. The evaporator means 56 includes a water chiller 64 having the evaporator cooling coils (not shown) operatively disposed therein, and cooling distribution means for selectively directing a variable portion of the cooling potential from the evaporator cooling coils to each of the alcohol condenser 28, the alcohol receiver tank 38, and to an external heat exchange load 66, such as a bulk milk container of the type commonly used on a dairy farm.

The cooling distribution means of the evaporator means 56 comprises a water supply or storage tank 68, and a pump 69 and water line 70 for circulating water from the tank 68 to the water chiller 64, and wherein the circulating water is cooled by heat exchange contact with the evaporator cooling coils. Thus the cooling potential of the refrigeration system is effectively stored in the water in the tank 68. The distribution means further comprises a second pump 72 and delivery line 73 from the tank 68, and which leads to a control valve 75. Three lines 76, 77, and 78 lead from the valve 75, with the line 76 leading to a coil 80 within the alcohol receiver tank 38 and back to the tank 68 through the return line 81. The line 77 leads to a coil 82 within the alcohol condenser 28 and back to the tank 68 through the return line 83, and the line 78 leads to a coil 85 which is operatively associated with the bulk milk container 66 and then leads back to the tank 68 through the return line 83. The control valve 75 is designed in a conventional manner so as to be able to direct a selected and variable amount of the cool water from the tank 68 through each of the lines 76, 77 and 78, or selected ones thereof.

In operation on a dairy farm, the refrigeration system and pump 69 are activated, causing the temperature of the condenser coil segments 61, 62 to rise, and with the cooling potential being delivered to the water which is passing through the chiller 64. The grain mash is fed into the preheater tank 12, where it absorbs heat from the coil segment 62. The thus heated mash then flows into the boiler tank 14, where it is boiled or vaporized by the heat from the coil segment 61. In this regard, it will be understood that the pressure in the boiler tank is reduced by the action of the vacuum pump 47, which is automatically operated to maintain a preselected partial vacuum within the receiver tank 38. The partial vacuum draws through the condenser 28, the separators 31, 32, and back to the boiler tank 14. Thus the boiling temperature of the mash may be reduced to a level where it can be effectively vaporized by the heat from the coil segment 61.

The vaporized alcohol passes through the pair of water separators 31, 32 and to the alcohol condenser 28. Typically, at least a portion of the cooling potential of the refrigeration system is delivered to the coil 82 in the condenser 28 by an appropriate setting of the valve 75 while the pump 72 is operating, to thereby cool and condense the alcohol. The amount of cool water delivered to the coil 82 in the condenser 28 is determined by a number of factors, including the volume of alcohol being processed, the magnitude of the external cooling load if any, and the availability of other independent cooling fluids, such as a natural cool water supply.

From the condenser 28, the condensed alcohol flows into the receiver tank 38, which serves as a storage receptacle for the alcohol. Since the tank 38 is maintained under a partial vacuum, it may be necessary to cool the alcohol in the receiver tank to prevent vaporization. In the illustrated embodiment, this cooling is accomplished by setting the valve 75 so that a portion of the cool water from the tank 68 passes through the coil 80. The distilled alcohol may then be periodically removed from the system through the drain line 44, either automatically or manually by monitoring the level of the alcohol in the sight glass 50. The resulting alcohol will typically be used as a fuel on the farm. Concurrently with the above operations, a portion of the cooling potential is directed to the bulk milk container 66 for cooling the milk produced by the dairy farm. Further, the distillation product (distillers grain) which is periodically removed from the tanks 12 and 14 may be fed to the cattle of the farm, without need to dry the product since it may be immediately consumed, and thus there is little risk of spoilage.

In the drawings and specification, there has been set forth a preferred embodiment of the invention, and although specific terms are employed, they are used in a generic and descriptive sense only and not for purposes of limitation.

That which is claimed is:

1. A method of distilling grain mash at a dairy farm or the like and characterized by the ability to efficiently utilize the required energy and the resulting products, and comprising the steps of providing distilland evaporating receptacle means, distillate condensing receptacle means, and a conduit operatively interconnecting the evaporating receptacle means and condensing receptacle means, providing a bulk milk container for containing milk, operating a vapor compression refrigeration system which comprises condenser coil means for producing heat energy and evaporator coil means for producing a cooling potential, and including directing at least a substantial portion of the heat energy of said condenser coil means to said evaporating receptacle means to heat and vaporize the distilland therein, and selectively directing the cooling potential from said evaporator coil means to either one or both of said condensing receptacle means and said bulk milk container, and recovering an alcoholic distillate from said condensing receptacle means.

2. The method of distilling grain mash as defined in claim 1 wherein said evaporating receptacle means comprises a preheater tank and a separate boiler tank, and means for conveying distilland into said preheater tank and from said preheater tank to said boiler tank.

3. The method of distilling grain mash defined in claim 2 wherein said condenser coil means of said refrigeration system comprises a first coil segment operatively associated with said boiler tank, and a second coil segment positioned downstream of said first segment and operatively associated with said preheater tank.

4. The method of distilling grain mash as defined in either one of claims 2 or 3 comprising the further step of providing water separating means operatively disposed in said conduit and drain means for returning the separated water from said separating means to said boiler tank.

5. The method of distilling grain mash as defined in any one of claims 1, 2, or 3 wherein said evaporator coil means includes an evaporator coil, and cooling distribution means for directing a selected and variable amount of the cooling potential from said coil to one or both of said condensing receptacle means and said bulk milk container.

6. The method of distilling grain mash as defined in claim 1 comprising the further step of providing condensate receiver means operatively connected to said condensing receptacle means to receive the condensate therefrom, and said evaporator coil means includes an evaporator coil, and cooling distribution means for directing a selected and variable amount of the cooling potential from said evaporator coil to each of said condensing receptacle means, said condensate receiver means, and said bulk milk container.

7. The method of distilling grain mash as defined in claim 6 comprising the further step of drawing a partial vacuum with said condensate receiver means such that the partial vacuum extends from said receiver means through said condensing receptacle means and to said evaporating receptacle means to lower the boiling temperature of the distilland in said evaporating receptacle means.

* * * * *